(12) United States Patent
Matolin et al.

(10) Patent No.: US 10,530,971 B2
(45) Date of Patent: Jan. 7, 2020

(54) PIXEL CELL CIRCUIT AND IMPLANT

(71) Applicants: PIXIUM VISION, Paris (FR); UNIVERSITE PIERRE ET MARIE CURIE (PARIS 6), Paris (FR); CENTRE NATIONAL DE LA RECHERCHE SCIENTIFIQUE-CNRS-, Paris (FR); INSERM (INSTITUT NATIONAL DE LA SANTÉ ET DE LA RECHERCHE MÉDICALE), Paris (FR)

(72) Inventors: Daniel Matolin, Chelmsford (GB); Christoph Posch, Bad Fischau (AT); Benjamin Ryad Benosman, Pantin (FR)

(73) Assignees: PIXIUM VISION, UNIVERSITE PIERRE ET MARIE CURIE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(\*) Notice: Subject to any disclaimer, the term of this patent is extended or adjusted under 35 U.S.C. 154(b) by 256 days.

(21) Appl. No.: 15/566,408

(22) PCT Filed: Apr. 6, 2016

(86) PCT No.: PCT/EP2016/057492
§ 371 (c)(1),
(2) Date: Oct. 13, 2017

(87) PCT Pub. No.: WO2016/165988
PCT Pub. Date: Oct. 20, 2016

(65) Prior Publication Data
US 2018/0078766 A1 Mar. 22, 2018

(30) Foreign Application Priority Data
Apr. 15, 2015 (EP) ..................... 15305563

(51) Int. Cl.
*H04N 5/14* (2006.01)
*A61N 1/05* (2006.01)
(Continued)

(52) U.S. Cl.
CPC ............. *H04N 5/14* (2013.01); *A61N 1/0543* (2013.01); *A61N 1/36046* (2013.01); *H04N 9/81* (2013.01)

(58) Field of Classification Search
CPC .......... H04N 5/14; H04N 9/81; A61N 1/0543; A61N 1/36046
See application file for complete search history.

(56) References Cited

U.S. PATENT DOCUMENTS

2013/0218271 A1  8/2013  Wu et al.

OTHER PUBLICATIONS

Benav et al., "Restoration of Useful Vision up to Letter Recognition Capabilities Using Subretinal Microphotodiodes," *32nd Annual International Conference of the IEEE EMBS*, IEEE, Buenos Aires, Argentina, Aug. 31-Sep. 4, 2010, pp. 5919-5922.
(Continued)

*Primary Examiner* — Lindsey G Wehrheim
(74) *Attorney, Agent, or Firm* — Seed IP Law Group LLP

(57) ABSTRACT

A pixel cell circuit comprises an electrode, one or more main photosensitive elements electrically coupled to the electrode for outputting a stimulation signal to the electrode responsive to light illumination, and a shunt arrangement comprising a shunt switch electrically coupled in parallel across the one or more photosensitive elements, and a control arrangement operatively coupled to the shunt switch and configured for placing the shunt switch in an open state responsive to incident light received at the pixel cell and placing the shunt switch in a closed state if no incident light is received at the pixel cell.

11 Claims, 2 Drawing Sheets

(51) Int. Cl.
    *A61N 1/36*    (2006.01)
    *H04N 9/81*    (2006.01)

(56) References Cited

OTHER PUBLICATIONS

Boinagrov et al., "Photovoltaic Pixels for Neural Stimulation: Circuit Models and Performance," *IEEE Transactions on Biomedical Circuits and Systems* 10(1):85-97, 2016.

Lichtsteiner et al., "A 128×128 120 dB 15 μs Latency Asynchronous Temporal Contrast Vision Sensor," *IEEE Journal of Solid-State Circuits* 43(2):566-576, 2008.

Loudin et al., "Photodiode Circuits for Retinal Prostheses," *IEEE Transactions on Biomedical Circuits and Systems* 5(5):468-480, 2011.

Mathieson et al., "Photovoltaic Retinal Prosthesis with High Pixel Density," *Nat. Photonics* 6(6):391-397, 2012. (18 pages).

Posch et al., "An Asynchronous Time-based Image Sensor," *IEEE International Symposium on Circuits and Systems*, IEEE, Seattle, Washington, May 18-21, 2008, pp. 2130-2133.

Posch et al., "A QVGA 143 dB Dynamic Range Frame-Free PWM Image Sensor With Lossless Pixel-Level Video Compression and Time-Domain CDS," *IEEE Journal of Solid-State Circuits* 46(1):259-275, 2011.

Wang et al., "Photovoltaic retinal prosthesis: implant fabrication and performance," *J Neural Eng.* 9(4):046014, 2012, 22 pages.

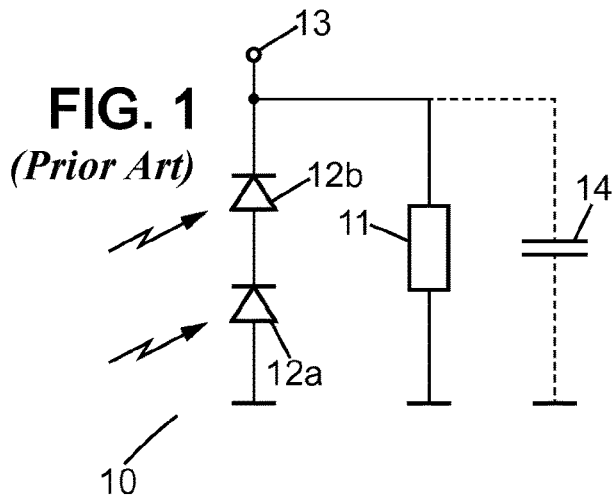
FIG. 1 *(Prior Art)*
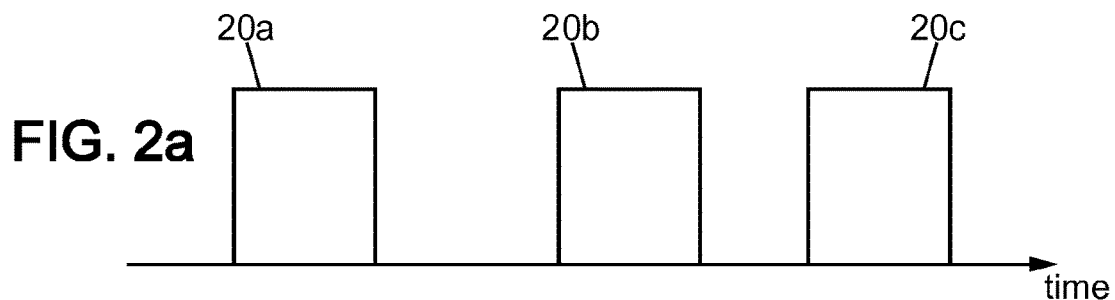
FIG. 2a
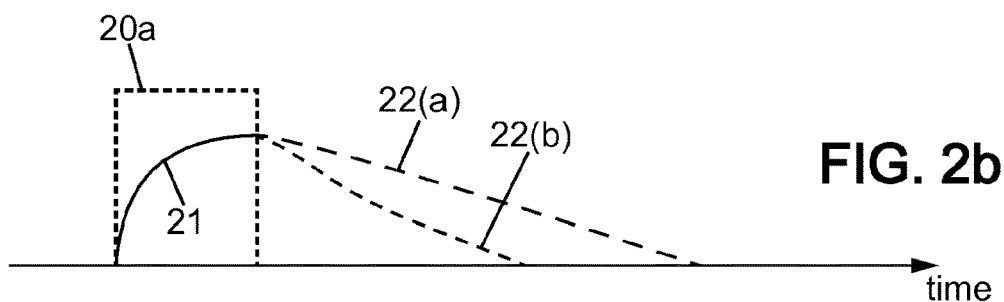
FIG. 2b
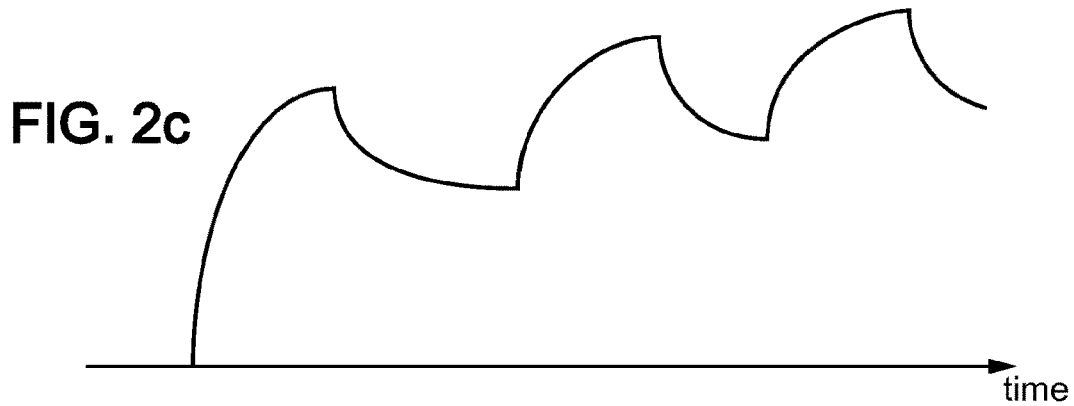
FIG. 2c

PIXEL CELL CIRCUIT AND IMPLANT

BACKGROUND

Technical Field

The present invention relates to microelectronics arrangements, in particular to a photosensitive pixel array and to an implant with such a pixel array.

Description of the Related Art

Retinal implant systems are known, which are able to at least partially restore vision to patients who have lost sight, for instance through degenerative diseases such as retinitis pigmentosa. Vision may at least to a certain degree be restored with an implant by exploiting the fact that the degenerated tissue of the retina may be bypassed and that the remaining retina cells may be stimulated electrically. This electrical stimulation can be provided by means of an implant system. It is well known that neural tissue can be artificially stimulated and activated by implants that pass pulses of electrical current through electrodes to neuronal cells. The passage of current causes changes in electrical potentials across neuronal cell membranes, which can initiate neuronal action potentials, which are the means of information transfer in the nervous system. Based on this mechanism, it is possible to input information into the nervous system by coding sensory information input as a sequence of electrical pulses which are relayed to the nervous system via the implant system. In this way, it is possible to provide artificially generated sensations including vision. Such a system typically comprises a head-mounted arrangement (e.g. in the form of goggles), which is placed in front of an eye of a patient, and an implant, in particular a sub-retinal implant, which comprises a plurality of electrodes.

In those goggles, typically a camera is provided. The camera is adapted to capture the visual scene in front of the patient. This captured scene information is processed by a computer and converted into a related light pulse signal. The implant is adapted to receive those light pulses and, in response, to convert light into electrical current that stimulates the residual cells in the retina.

For that purpose, the implant comprises an array of electrically isolated pixels, wherein each pixel comprises one or more photosensitive elements such as photodiodes and a stimulating electrode. The photosensitive elements receive the light pulses and convert the information carried by the light input into electrical signals that are conveyed to the electrodes.

An example of retinal implant including photosensitive pixel array is described in Mathieson et al., "Photovoltaic retinal prosthesis with high pixel density", Nat Photon, vol. 6, pp. 391-397, 2012. In such a system, the implant includes an array of pixel cells, each pixel cell implementing a microelectronics circuit with an optical receiver pixel array of photodiode elements for converting received pulsed near-IR (~900 nm) light into biphasic pulses of electric current able to stimulate retinal neurons. Although an array of pixel cells can be limited to a single cell, it will generally include a number of pixel cell circuits corresponding to a desired spatial resolution for stimulation of the eye's tissue.

In order to improve performance of these implants including photosensitive pixel array, for example by increasing quality of retina stimulation, temporal or spatial resolution, visual acuity, etc., it has been proposed to increase the achievable light pulse repetition rate beyond state-of-the-art rates of about 30 Hz, possibly towards the native temporal resolution of retinal cells of the order of 1000 Hz or higher.

The light-sensitive (or photosensitive) elements in microelectronic implementations of state-of-the-art retinal implants are realized in the form of semiconductor photodiodes. The electrical circuit composed of the stimulation electrodes and the photodiodes entails (parasitic) capacitances that are alternately charged and discharged by currents flowing in and out these capacitances. The charging phase (when the light pulse turns ON) is dependent on the light-induced photocurrent whereas the discharge (light is OFF) depends on currents flowing through the high-impedance path via the tissue to a return electrode. Due to this impedance limiting discharge currents to values much smaller than the photocurrents, the discharge time can become long compared to the charging time.

An incomplete discharge at the time of another stimulation light pulse arriving at the same implant pixel decreases the achievable charge injection of this second stimulation pulse and therefore limits the stimulation efficiency of the implant pixel. As a consequence, the repetition rate of stimulation light pulses sent to one implant pixel becomes limited if a certain minimum stimulation efficiency is to be retained, impacting the achievable temporal resolution of stimulation. (see Loudin et al., 2011, IEEE Transaction on Biomedical Circuits and Systems, 5, 468-480). It appears that actually, the photovoltaic current (and thereby stimulation efficiency) decreases exponentially with increasing light pulses frequency (Loudin et al., 2011, supra). To speed-up discharge of the electrode between the light pulses and thereby avoid charge accumulation and the associated decrease of current with consecutive pulses, it has been proposed to add a shunt resistor. For example, Wang et al. (2012, J. Neural Eng., 9, 1-11) describe that the addition of a shunt resistor will help to speed up the discharge phase of the stimulation waveform or Loudin et al. (2011, IEEE Transaction on Biomedical Circuits and Systems, 5, 468-480) suggest the use of a shunt resistor for photodiode circuits in retinal prostheses. The shunt resistor allows the charge delivered during the first phase of the light pulse to be more rapidly discharged but also impacts the charge, which is actually delivered to the tissue. It has been shown for example that if resistance of the shunt resistor is too high, the electrodes will not completely discharge between the pulses and that the accumulation of charge on the electrode will reduce the amount of charge delivered during the successive pulses. As a result, there exists a trade-off between achievable stimulation efficiency and temporal resolution of stimulation as long as a fixed-value resistor is used as the shunt device. As a consequence, in state-of-the-art implementations, the shunt resistor value is optimized for a certain compromise between these two conflicting parameters. (Boinagrov et al., *Photovoltaic Pixels for Neural Stimulation: Circuit Models and Performance,* January 2015, IEEE Transactions on Biomedical Circuits and System).

Therefore there is still a need for providing an improved pixel cell circuit and implants, such as photovoltaic visual implants, incorporating the same that address the above-described drawbacks and allows stimulation with light pulses rates beyond about 30 Hz, more specifically beyond about 50 Hz, and even more specifically beyond about 100 Hz without decreasing electrode stimulation efficiency. In other words, there is a need for microelectronics arrangements that will break the detrimental interdependence between achievable stimulation pulse repetition rate and stimulation efficiency.

BRIEF SUMMARY

It is therefore a specific object of the present invention to provide an optimized pixel cell circuit with respect to light pulse repetition rates which addresses this need. The approach taken to achieve this goal is to replace the fixed-value shunt resistor with a variable resistor that automatically adapts is resistance depending on the state of the stimulation process.

The present invention further provides an implant, such as visual implant, incorporating or implementing said optimized pixel cell circuit.

The problem is solved according to the invention with a pixel cell circuit according to independent claim 1. Advantageous developments are subject-matter of the dependent claims.

Preferably, the present invention provides a pixel cell circuit that can be operated with light pulses rates beyond about 30 Hz, more specifically beyond about 50 Hz, and even more specifically beyond about 100 Hz.

The present invention further provides an implant, such as visual implant, incorporating or implementing said pixel cell circuit that can be operated with light pulses rates beyond about 30 Hz, more specifically beyond about 50 Hz, and even more specifically beyond about 100 Hz.

The present invention further provides a pixel cell circuit and implants, such as visual implants incorporating or implementing the same, that can be operated with light pulses rates of about 1000 Hz.

According to an embodiment of the present invention, it is provided a pixel cell circuit which comprises one or more main photosensitive element, at least one electrode, preferably, a stimulating electrode, and a shunt arrangement comprising:

(i) a shunt switch electrically coupled in parallel across the one or more main photosensitive element, and (ii) a control arrangement operatively coupled to the shunt switch and configured for placing the shunt switch in an open state responsive to incident light received at the pixel cell and placing the shunt switch in a closed state if no incident light is received at the pixel cell.

The inventors have now shown that using a shunt arrangement according to the invention allows to approach the ideal situation of having a shunt resistor with close to infinite resistance at the light input onset phase, and close to zero resistance at the discharge phase, thereby maximizing charge transfer efficiency and minimizing discharge rate that limits the light pulse repetition rate observed in prior art.

According to a special embodiment, the shunt switch is implemented as a MEMS (micro-electromechanical-systems) or NEMS (nano-electromechanical-systems) device.

According to another special embodiment, the shunt switch is a semiconductor-based active component, such as for example a transistor. According to a specific embodiment, it is implemented in the form of a FET (field-effect transistor, such as for example a metal-oxide semiconductor (MOS) transistor) or in the form of a bipolar transistor.

According to another special embodiment, the control arrangement is configured for placing the shunt switch in an open state responsive to incident light received at the one or more main photosensitive element and placing the shunt switch in a closed state if no incident light is received at the one or more main photosensitive element.

According to another special embodiment, the control arrangement comprises an auxiliary photosensitive element, and is configured for placing the shunt switch in an open state responsive to incident light received at the said auxiliary photosensitive element and placing the shunt switch in a closed state if no incident light is received at the said auxiliary photosensitive element.

According to another special embodiment, the control arrangement comprises a switch control arrangement, a power supply arrangement configured for supplying power to the switch control arrangement, and a timing control arrangement configured for generating a timing signal to the switch control arrangement, wherein the switch control arrangement is configured for controlling the operation of the shunt switch based on the said timing signal.

According to another special embodiment, the said power supply arrangement comprises a storage capacitor electrically coupled to a reference potential of the pixel circuit on the one end, and to a node connecting the electrode and the one or more main photosensitive element through another switch on the other end, and the switch control arrangement is further configured for controlling the operation of the supply switch based on the timing signal.

According to another special embodiment, the timing control arrangement comprises an auxiliary photosensitive element electrically coupled in series to a load, wherein the load is electrically coupled to a node connecting the electrode and the one or more main photosensitive element.

According to another special embodiment, the switch control arrangement is configured for opening the shunt switch then closing the supply switch responsive to the timing signal indicating that incident light is received at the pixel cell, and for opening the supply switch then closing the shunt switch responsive to the timing signal indicating that incident light is no longer received at the pixel cell.

According to one specific embodiment, said pixel cell circuit further comprises at least one counter electrode, also referred to as return electrode, According to a further development of the present invention, the counter electrode is arranged around the stimulating electrode. In addition or alternatively, the counter electrode may be arranged around the at least one photosensitive element. The term "arranged around" in the context of the present invention shall be understood such that the counter electrode has a lateral dimension and, in that lateral dimension, extends around the area defined by the stimulating electrode or by the at least one photosensitive element. In the case that a plurality of photosensitive element is provided, the counter electrode may be arranged around one or all of the photosensitive element. Preferably, the counter electrode is arranged symmetrically around the stimulating electrode.

According to another special embodiment, photosensitive elements are selected in the group consisting of photodiode photodiodes, phototransistors, photoresistors or other photosensitive semiconductor devices.

According to a preferred embodiment, the main photosensitive element(s) and the auxiliary photosensitive element are implemented in the form of semiconductor photodiodes.

According to another special embodiment, the present invention provides a pixel cell circuit as disclosed herein implemented using complementary metal oxide semiconductor (CMOS) fabrication technology compatible components.

According to a further aspect of the present invention, an implant is provided with a photosensitive pixel array wherein said array comprises at least one pixel cell circuit according to the invention. By providing a photosensitive pixel array to the implant, the implant is rendered a photosensitive implant, which may provide electrical stimulation to neural tissue. In particular, the implant may allow electrical stimulation to retina tissue of an eye of a subject. Alternatively, the implant of the invention may allow electrical stimulation to any neuronal tissue of a subject as far as the implant is localized such that light exposure is possible (transparent tissues, . . . ).

In a preferred embodiment, the implant is a sub-retinal implant. That allows positioning the implant within the eye of a patient, i.e. sub-retinally, in order to bypass any damaged tissue of the retina. Consequently, the electrical impulses may be generated in close proximity to the sensitive neural cells which are still functional in the retina. Advantageously, the photosensitive implant also comprises a sealing layer or a sealing coating, in order to protect the implant structure from either of corrosion or damage.

Another aspect of the invention is a visual prosthesis comprising an implant of the invention and a camera.

Another aspect of the present invention is a method of neural stimulation, comprising: implanting an implant of the invention close to neural tissue and stimulating said neural tissue according to light pulses rates beyond about 30 Hz, more specifically beyond about 50 Hz, and even more specifically beyond about 100 Hz. Typically, a light pulse is an infrared light pulse.

It should be appreciated that the present invention can be implemented and utilized in numerous ways, including without limitation as a process, an apparatus, a system, a device, and as a method for applications now known and later developed. These and other unique features of the invention disclosed herein will become more readily apparent from the following description and the accompanying drawings.

BRIEF DESCRIPTION OF THE SEVERAL VIEWS OF THE DRAWINGS

Further details, preferred embodiments and advantages of the present invention will be found in the following description with reference to the drawings, in which:

FIG. 1 is a schematic diagram illustrating a pixel cell circuit using a shunt resistor;

FIGS. 2a, 2b, and 2c illustrate a train of light pulses and current pulses generated by the pixel cell circuit of FIG. 1;

DETAILED DESCRIPTION

Figure 3:
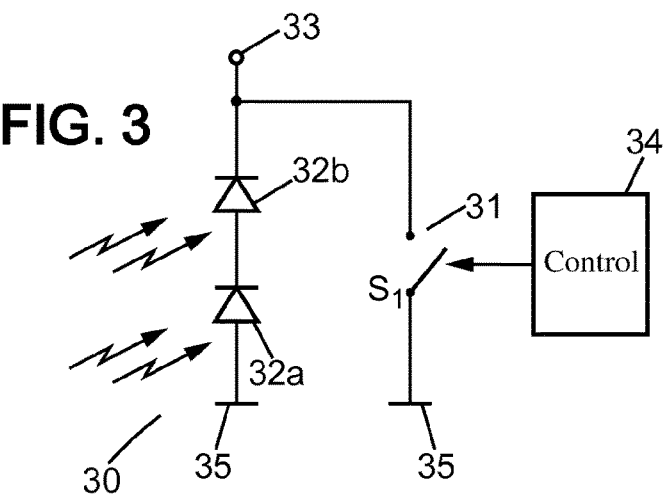
FIG. 3 is a schematic diagram illustrating a pixel cell circuit according to the present invention.

For simplicity and clarity of illustration, the figures illustrate the general manner of construction, and descriptions and details of well-known features and techniques may be omitted to avoid unnecessarily obscuring the discussion of the described embodiments of the invention.

Additionally, elements in the figures are not necessarily drawn to scale. For example, the dimensions of some of the elements in the figures may be exaggerated relative to other elements to help improve understanding of embodiments of the present invention. Certain figures may be shown in an idealized fashion in order to aid understanding, such as when structures are shown having straight lines, sharp angles, and/or parallel planes or the like that under real-world conditions would likely be significantly less symmetric and orderly.

The same reference numerals in different figures denote the same elements, while similar reference numerals may, but do not necessarily, denote similar elements.

In addition, it should be apparent that the teaching herein can be embodied in a wide variety of forms and that any specific structure and/or function disclosed herein is merely representative. In particular, one skilled in the art will appreciate that an aspect disclosed herein can be implemented independently of any other aspects and that several aspects can be combined in various ways.

The terms "comprise," "include," "have," and any variations thereof, are intended to cover a non-exclusive inclusion, such that a process, method, article, or apparatus that comprises a list of elements is not necessarily limited to those elements, but may include other elements not expressly listed or inherent to such process, method, article, or apparatus.

The word "exemplary" is used herein to mean "serving as an example, instance, or illustration". Any embodiment or design described herein as "exemplary" is not necessarily to be construed as preferred or advantageous over other embodiments or designs.

In the following description and claims, the terms "coupled" and "connected", along with their derivatives, may be used. In particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other.

FIG. 1 shows an exemplary conventional photodiode pixel circuit (10) that uses a shunt resistor (11). Shown on FIG. 1 two photodiode elements (12a, 12b) are electrically coupled in series, with one photodiode electrically coupled to a reference potential e.g. connected to the return electrode, and the other photodiode connected to a stimulation electrode (13). The shunt resistor (11) is mounted parallel to the photodiode elements (12a, 12b), so as to decrease the discharge time of the parasitic capacitance (14) (represented with dashed lines on the figure) of the photodiode elements (12a, 12b) and the stimulation electrode (13).

FIG. 2a shows a train of ideal square-shaped light pulses used for stimulation of a photodiode pixel circuit of the type shown on FIG. 1. The single light pulses used for stimulation of the pixels of the retinal implant may have variable amplitudes, variable pulse widths and variable onset times with respect to the previous pulse. When exposed to a light stimulation in the form of a light pulse such as represented in FIG. 2a, currents start flowing through the stimulation photodiodes (12a, 12b), delivering an electrical charge to the tissue via the electrode. FIG. 2b illustrates the voltage across the stimulation photodiodes (12a, 12b), which increases from a rest level, e.g. a zero or near-zero level, to a maximum level depending on the characteristics of the photodiode elements (12a, 12b) and the value of the shunt resistor (11).

At the end of a light pulse, the photodiode elements stop receiving light and the voltage across the photodiode elements (12a, 12b) starts decreasing towards the rest level. The time constant of this decay is depending on the (parasitic) capacitances (14), mainly appearing at the electrode (13) and the photodiodes (12a, 12b), and the value of the shunt resistor. The decay time constant becomes maximally slow in the absence of a shunt resistor.

Therefore a phase of increase (21) of the voltage across the stimulation photodiodes (12a, 12b) during light stimulation thereof is followed by a phase of decrease (22a) of the same voltage, responsive to the end of the light pulse (20a), that is, the end of the light stimulation of the photodiode elements (12a, 12b). The duration of the decrease phase (22a) corresponds in part to the discharge time of the parasitic capacitance (14). This discharge time may be decreased by the operation of a shunt resistor, such as the one (11) shown on FIG. 1, which functions as a current path capturing some of the current, which otherwise would partly flow through the electrode (13) and the neural tissue (effecting stimulation) during the increase phase (21), and discharge the parasitic capacitance (14) during the decrease phase (22b).

FIG. 2a further shows a second light pulse (20b) following the first light pulse (20a) in the train of light pulses (20a, 20b, 20c), and spaced therefrom by a time duration which is smaller than the decrease time corresponding to the decrease phase (22b) when using the shunt resistor (11). This second light stimulation therefore starts before the voltage across the stimulation photodiodes (12a, 12b) returns to the rest level, i.e. before the end of the voltage decrease phase (22b).

The remaining higher voltage level across the stimulation photodiodes (12a, 12b) at the onset of the second light pulse (20b) results in a decrease of current through the stimulation photodiodes (12a, 12b) and through the electrode (13) in response to the second light pulse (20b), and therefore in a reduced current available for stimulation of the neural tissue.

FIG. 2a also shows a third light pulse (20c) following the second light pulse (20b) in the train of light pulses (20a, 20b, 20c), and spaced therefrom by a time duration which is smaller than the decrease time corresponding to the decrease phase (22b) when using the shunt resistor (11). As illustrated in FIG. 2c, the available stimulation current is further reduced due to a further increased voltage across the stimulation photodiodes (12a, 12b) at the onset of the third light pulse (20c). Therefore, the repetition rate of the light pulses for stimulation is limited by the decrease phase (22b) if a certain stimulation current amplitude needs to be retained, which constitutes a limitation of the pixel circuit (10).

In addition, the use of a fixed-value ohmic resistor-based shunt raises the issue of the determination of the ohmic value of the shunt resistor(s). The choice of a value for a shunt resistor will be the result of a trade-off between the rate at which stimulation pulses can be applied, which can be increased by decreasing the value of the shunt resistor, and the stimulation efficiency. The lower the chosen ohmic value for the shunt resistor, the more current will flow through the shunt resistor during a light stimulation pulse, at the expense of electrode stimulation efficiency. Inversely, the higher the chosen ohmic value for the shunt resistor, the less current will flow through the shunt resistor, including during a parasitic capacitance discharge phase, thereby increasing the discharge time.

This shows that the pixel circuit (10) which uses a shunt resistor may not be adapted for applications which require a high temporal resolution or a high stimulation rate. For example, when visual scene data are captured using an event-based vision sensor of the ATIS (« Asynchronous, Time-Based Image Sensor») type, such as the one described in « An Asynchronous Time-based Image Sensor» (C. Posch et al., IEEE International Symposium on Circuits and Systems, 2008, pages 2130-2133), or in « A QVGA 143 dB dynamic range frame-free PWM image sensor with lossless pixel-level video compression and time-domain CDS» (C. Posch et al., 46(1):259275, 2011), a projector device coupled to the ATIS camera output may generate a train of light pulses with a temporal resolution as high as 1 millisecond (or temporary stimulation rates as high as 1000 Hz).

More generally, recent research has shown that increasing the possible stimulation rates beyond state-of-the-art rates of about 30 Hz towards the native temporal resolution of retinal cells of the order of 1000 Hz could greatly improve the quality of retina stimulation.

FIG. 3 shows a photodiode pixel circuit according to the invention which uses a shunt switch arrangement in place of the shunt resistor shown in FIG. 1.

In one or more embodiments, the shunt switch arrangement may be implemented using active semiconductor-based devices such as, for instance, a transistor device (e.g. FET transistor or bipolar transistor). In such embodiment, the gate or base of a transistor used in the shunt switch arrangement may be controlled in phase with the stimulating light pulse.

Alternatively, the shunt switch arrangement may be provided in the form of a micro-electromechanical-systems (MEMS) device or a nano-electromechanical-systems (NEMS) device, such as, for instance, a micro-mechanical switch designed to achieve a short circuit or an open circuit in a shunt line electrically coupled in parallel to one or several photovoltaic photodiodes.

In one or more embodiments, the timing of the operation of the shunt switch arrangement may be implemented using a control signal carrying timing information derived from the light input to the pixel. In some embodiments, such a control signal may be generated using an additional small photodiode. Alternatively, or in addition, timing information carried by the control signal may be derived from the current flowing through the main photodiodes.

Shown in FIG. 3 are two photodiode elements (32a, 32b) electrically coupled in series, with one photodiode electrically coupled to a reference potential (35), e.g. connected to the return electrode, and the other electrically coupled to a pixel circuit electrode (33). The photodiode elements (32a, 32b) are arranged to receive light and translate impinging light into stimulation currents from the electrode through the tissue. It will be appreciated by those having ordinary skill in the relevant art that any suitable light transducer device converting incident light into an electric signal may be used in place of the photodiode elements (32a, 32b), which are given by way of example only.

In addition, the present invention is not limited to a specific arrangement of photodiode elements or photosensitive element, and embodiments thereof may use a single photodiode element, or a combination of two or more elements. Switch S1 (31) is a shunt device provided for decreasing the discharge time of parasitic capacitances of the circuit (30), and in particular the electrode (33) and the photodiode elements (32a, 32b), as well as increasing the stimulation efficiency of the tissue through the electrode (33), and is mounted parallel to the photodiode elements (32a, 32b). A control arrangement (34) is provided with the switch S1 (31) for controlling the operation thereof, including a power supply.

The advantage of a switch provided as a shunt device over a fixed ohmic shunt resistor is that it can approach the ideal situation of having infinite resistance at the light input onset phase, and zero resistance at the discharge phase, so that it can both maximize charge transfer efficiency and minimize discharge time that limits the repetition rate of stimulation current pulses transmitted to the tissue through the electrode (33). As discussed above, the use of a fixed ohmic shunt resistor requires the determination of an ohmic value of the resistor, which value will reflect a compromise between stimulation efficiency and repetition rate. This compromise can be advantageously overcome by using a switching device to provide the shunt.

In operation, the control arrangement (34) is designed so as to place the switch S1 (31) in the open state, thereby achieving a high resistance in the switch S1 (31) line, responsive to reception of incident light at the photodiode elements (32a, 32b), and to place the switch S1 (31) in the closed state, thereby achieving a low resistance in the switch S1 (31) line, responsive to the lack of reception of incident light at the photodiode elements (32a, 32b).

Stimulation is initiated by delivering light to the photodiode elements (32a, 32b), for instance by switching on a light source that delivers light to the circuit (30). Responsive to the reception of light at the photodiode elements (32a, 32b), current starts flowing through the photodiode elements (32a, 32b), delivering charge to the tissue via the electrode (33). The control arrangement (34) is designed to open switch S1 (31), so as to prevent part of the current delivered by the photodiode elements (32a, 32b) from flowing through the shunt path (instead of through the tissue) to the return electrode, and consequently this part of the charge not participating in the stimulation. Because the shunt switch is mounted parallel to the photodiode elements the control arrangement is preferably configured in some embodiments so as to open switch S1 (31) shortly after current starts flowing through the photodiode elements (32a, 32b). Likewise, it may be preferable in some embodiments to configure the control arrangement so that it closes switch S1 (31) shortly after an end of reception of incident light at the photodiode elements (32a, 32b). For example, when the circuit (30) is stimulated with light pulses, the control arrangement may preferably be configured in some embodiments so as to place the shunt switch in the open state shortly after a stimulation light pulse arrives, and to place the shunt switch in the closed state shortly after the stimulation light pulse ends and to keep the switch in this state long enough so as to allow a complete discharge of the parasitic capacitances of the circuit (30).

Therefore in some embodiments, the timing of the operation of the shunt switch S1 (31) may be achieved using the current flowing through, that is, through light input to the photodiode elements (32a, 32b) which are the main light transducer elements configured for receiving the light stimulation to which the photodiode pixel circuit (30) is exposed.

In some other embodiments, the timing of the operation of the shunt switch S1 (31) may, as an alternative or in addition to using the current flowing through the photodiode elements (32a, 32b) as a result of light input thereto, be achieved using an additional small photodiode, which will preferably be placed in close proximity to the other photodiodes, that is, in the exemplary embodiment shown on FIG. 3, close to the photodiode elements (32a, 32b).

Depending on the embodiment, various ways of supplying power to the switch S1 (31) and the control arrangement (34) may be implemented. In the specific context of a pixel circuit implemented in implant comprising photosensitive element, such as photodiode elements, it is advantageous in some embodiments to use supply voltage delivered by the photosensitive element themselves.

Figure 4:
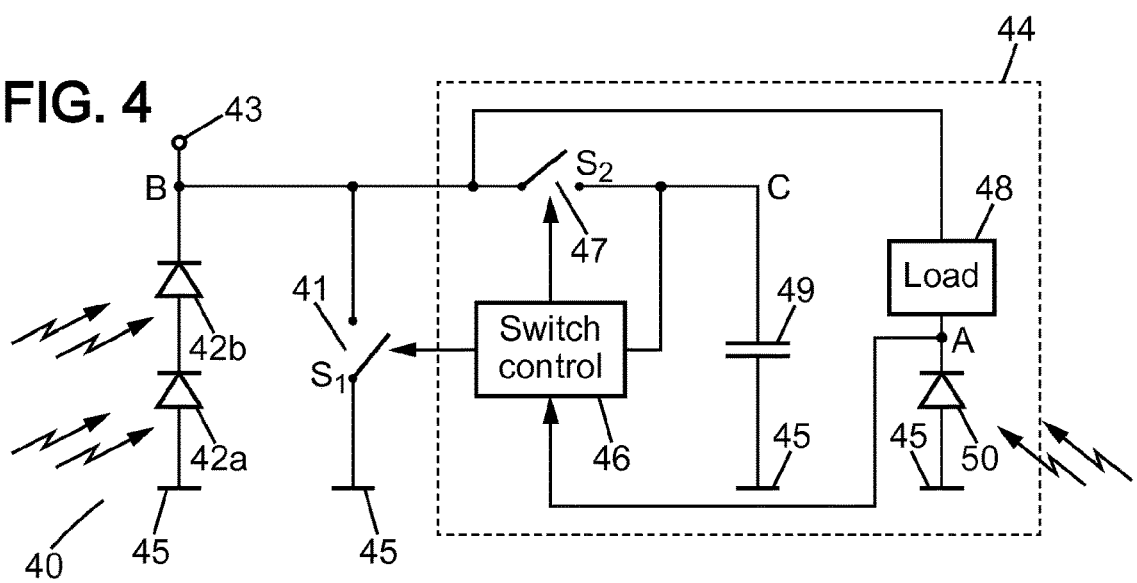
FIG. 4 is a schematic diagram illustrating a pixel cell circuit according to the present invention.

FIG. 4 shows a photodiode pixel circuit (40) according to an exemplary embodiment including a control arrangement where the supply voltage is provided by the photosensitive element.

Shown on FIG. 4, two photodiode elements (42a, 42b) are electrically coupled in series, with one photodiode electrically coupled to a reference potential (45), e.g. connected to the return electrode, and the other electrically coupled to a pixel circuit electrode (43). The photodiode elements (42a, 42b) are arranged to receive light and translate impinging light into stimulation currents from the electrode through the tissue. It will be appreciated by those having ordinary skill in the relevant art that any combination of one or more of any suitable photosensitive element converting incident light into an electric signal may be used in place of the photodiode elements (42a, 42b), which are given by way of example only.

Similar to the circuit illustrated on FIG. 3, switch S1 (41) is a shunt device mounted parallel to the photodiode elements (42a, 42b). A control arrangement (44) is provided with the switch S1 (41) for controlling the operation thereof, including a power supply. The control arrangement (44) includes a switch control (46), a power supply arrangement for supplying power to the switch control (46) in the absence of light, and a timing control arrangement.

The power supply arrangement comprises a second switch S2 (47) and a storage capacitor (49), electrically coupled in series, with one end of the storage capacitor (49) electrically coupled to the reference potential (45) and the other end electrically coupled to one end of the switch S2 (47), while the other end of the switch S2 (47) is electrically coupled to the photodiode elements (42a, 42b), for example to the node (B) between the photodiode elements (42a, 42b) and the electrode (43).

The timing control arrangement is used for controlling the timing of the operations of the shunt switch S1 (41) and of the second switch S2 (47), and comprises an auxiliary photodiode element (50) (or, depending on the embodiment, any suitable light transducer device) electrically coupled to the reference potential (45) on the one end, and to a load (48) on the other end. The auxiliary photodiode (50) is further electrically coupled to the switch control (46) through an electrical connection between a node (A) located in-between the auxiliary photodiode (50) and the load (48), and the switch control (46). The other end of the load is electrically coupled to the photodiode elements (42a, 42b), for example to the node (B) between the photodiode elements (42a, 42b) and the electrode (43).

The switch control (46) is configured for controlling the operations of the shunt switch S1 (41) as well as that of the second switch S2 (47), based on the timing signal received from the timing control arrangement.

The circuit illustrated in FIG. 4 is designed so that any active electrical circuitry of the photodiode pixel circuit (40) is powered by the voltage generated by the main photosensitive element, that is, the photodiode elements (42a, 42b), in the presence of light. In order for the circuit (40) to be active also at times where no light shines onto the main photosensitive element (42a, 42b), a supply voltage is generated at least for some time after light has ceased impinging on the photosensitive element (42a, 42b). In the exemplary embodiment illustrated in FIG. 4, this is achieved using one or several storage capacitors (49). It will be appreciated by those having ordinary skill in the relevant art that any suitable device or component can be used in place of the storage capacitor (49), which is given by way of example only.

In some embodiments, in case the voltage generated by the main photosensitive element (42a, 42b) is insufficient to or otherwise not suitable for powering the shunt control arrangement, a suitable supply voltage may be generated in the pixel, for example by employing a charge-pump circuit (not represented on the figure).

During operation, a stimulation cycle corresponding to a stimulation light pulse of the type of that illustrated on FIG. 2a, is initiated by switching on a light source that delivers light to the circuit (40). Currents start flowing through the stimulation photodiodes (42a, 42b), delivering charge to the tissue via the electrode (43). At the same time, current flowing through the auxiliary photodiode (50) results in the voltage at the node (A) between the photodiode (50) and its load (48) to drop to a level near the reference potential, as the auxiliary photodiode behaves like an ideal current source electrically coupled to the reference potential (45). As the control block (46) is electrically coupled to the node (A) located between the auxiliary photodiode (50) and its load (48), the control block (46) receives the voltage at node (A) as a control signal. The switch control block (46), in response to the voltage at node (A) dropping to a level close to the reference potential, opens switch S1 (41) and closes switch S2 (47). The storage capacitor (49) consequently gets charged to the voltage developing across the photovoltaic stimulation photodiodes (42a, 42b), that is, in the figure, the voltage at the node (B) located between the load (48) and the electrode (43), as the storage capacitor (49) is electrically coupled to the reference potential (45) at one end, and electrically coupled to node (B) at the other end through the closed switch S2 (47).

At the end of the stimulation, light is switched off and the parasitic capacitances of the circuit (40), and in particular of the photovoltaic stimulation photodiodes (42a, 42b) and the electrode (43), should be discharged as quickly as possible in order to get ready for the next stimulation cycle.

In the absence of light stimulation, the auxiliary photodiode (50) behaves as an open circuit (said otherwise a current source with nil current), so that the voltage at node (A) located between the auxiliary photodiode (50) and its load (48) increases to reach again the voltage at node (B) located between the load (48) and the electrode (43). The switch control (46) detects the changes of voltage at node (A), through the line coupling the switch control (46) to node (A), and switch S1 (41) is closed by the switch control circuit, resulting in the voltage across the photovoltaic stimulation photodiodes (42a, 42b) to collapse. This achieves a fast discharge of the parasitic capacitances of the photovoltaic stimulation photodiodes (42a, 42b) and the electrode (43).

In order to continue the operation of the switch control circuit at this stage using the storage capacitor (49), the switch control (46) has opened switch S2 (47) briefly before closing switch S1 (41), effectively preventing the storage capacitor (49) from also being discharged through switch S1 (41). From this point in time (after opening switch S2 (47)), electrical power to the switch control block is supplied by the storage capacitor (49). For this, the power supply terminal of the switch control block is electrically coupled to the one side of the storage capacitor (node (C)) that is not coupled to the reference potential (45). The timing for the operation of the switches S2 (47) and S1 (41) is derived from the switching of the voltage at node (A) above the auxiliary photodiode (50) that rises quickly after the light has switched off. After the end of the discharge phase, the circuit (40) settles to an idle state and is ready to receive a new stimulation light pulse that restarts the process described above.

Figure 5:
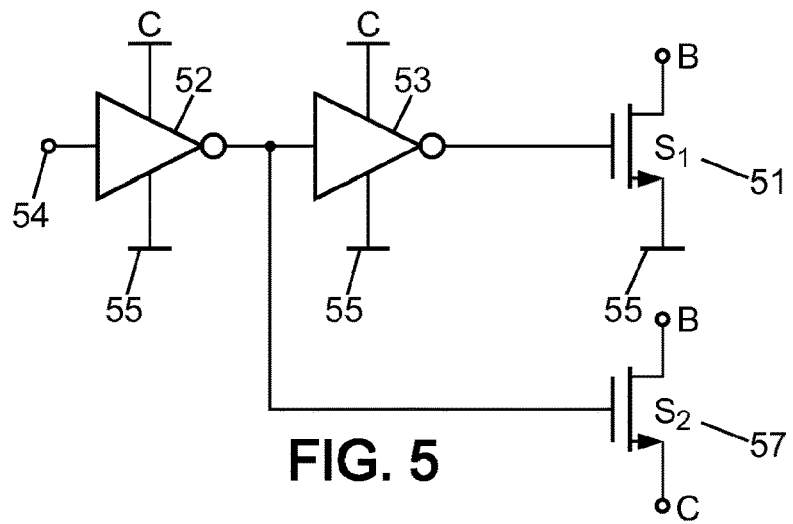
FIG. 5 shows an exemplary embodiment of a switch control block according to an embodiment of the present invention.

FIG. 5 shows an exemplary embodiment of the switch control block (46 in FIG. 4). The input node (54) of the switch control block is connected to node (A) of FIG. 4 such that the voltage at this node drives the input of a logic inverter (52). The output of this inverter is connected to control the switch S2 (57, or 47 in FIG. 4) implemented as a NMOS (N-channel MOSFET) transistor where the drain of this transistor is connected to node (B) and the source is connected to node (C). The output of the same inverter (52) is also connected to the input of a second inverter (53). The output of this second inverter (53) is connected to control the switch S1 (51, or 41 in FIG. 4) implemented as a NMOS transistor where the drain of this transistor is connected to node (B) and the source is connected to a reference potential (55, or 45 in FIG. 4). The power supply connections of both inverters (52, 53) are connected to node (C) and the ground connection of both inverters (52, 53) are connected to a reference potential (55, or 45 in FIG. 4).

While the invention has been described with respect to preferred embodiments, those skilled in the art will readily appreciate that various changes and/or modifications can be made to the invention without departing from the spirit or scope of the invention as defined by the appended claims.

Although this invention has been disclosed in the context of certain preferred embodiments, it should be understood that certain advantages, features and aspects of the systems, devices, and methods may be realized in a variety of other embodiments. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred embodiments.

Information and signals described herein can be represented using any of a variety of different technologies and techniques. For example, data, instructions, commands, information, signals, bits, symbols, and chips can be represented by voltages, currents, electromagnetic waves, magnetic fields or particles, optical fields or particles, or any combination thereof.

Depending on the embodiment, certain acts, events, or functions of any of the methods described herein can be performed in a different sequence, may be added, merged, or left out altogether (e.g., not all described acts or events are necessary for the practice of the method). Moreover, in certain embodiments, acts or events may be performed concurrently rather than sequentially.

The invention claimed is:

1. A pixel cell circuit comprising:
an electrode;
at least one main photosensitive element electrically coupled to the electrode for outputting a stimulation signal to the electrode in response to light illumination;
a shunt arrangement comprising:
a shunt switch electrically coupled in parallel across the at least one main photosensitive element, and
a control arrangement operatively coupled to the shunt switch and configured to place the shunt switch in an open state responsive to incident light received at the pixel cell circuit and place the shunt switch in a closed state if no incident light is received at the pixel cell circuit.

2. The pixel cell circuit according to claim 1, wherein the shunt switch is one of a micro-electromechanical system device, a nano-electromechanical system device, and a semiconductor-based active component.

3. The pixel cell circuit according to claim 1, wherein the shunt switch is a semiconductor-based active component selected from a group that includes field-effect transistors and bipolar transistors.

4. The pixel cell circuit according to claim 1, wherein the control arrangement is configured to place the shunt switch in the open state responsive to incident light received at the at least one main photosensitive element and place the shunt switch in the closed state if no incident light is received at the at least one main photosensitive element.

5. The pixel cell circuit according to claim 1, wherein the control arrangement comprises an auxiliary photosensitive element, and is configured to place the shunt switch in the open state responsive to incident light received at the auxiliary photosensitive element and place the shunt switch in the closed state if no incident light is received at the auxiliary photosensitive element.

6. The pixel cell circuit according to claim 1, wherein the control arrangement comprises:
 a switch control arrangement;
 a power supply arrangement configured to supply power to the switch control arrangement;
 a timing control arrangement configured to generate a timing signal to the switch control arrangement;
 wherein the switch control arrangement is configured to control the shunt switch based on the timing signal.

7. The pixel cell circuit according to claim 6, wherein the electrode and the at least one main photosensitive element are connected to each other by a node and the power supply arrangement comprises:
 a supply switch; and
 a storage capacitor having a first terminal electrically coupled to a reference potential of the pixel circuit, and a second terminal electrically coupled to the node through the supply switch, wherein the switch control arrangement is further configured to control the supply switch based on the timing signal.

8. The pixel cell circuit according to claim 7, wherein the switch control arrangement is configured to open the shunt switch then close the supply switch responsive to the timing signal indicating that incident light is received at the pixel cell circuit, and to open the supply switch then close the shunt switch responsive to the timing signal indicating that incident light is no longer received at the pixel cell circuit.

9. The pixel cell circuit according to claim 6, wherein the timing control arrangement comprises an auxiliary photosensitive element and a load electrically coupled to each other in series, wherein the load is electrically coupled to a node connecting the electrode and the at least one main photosensitive element.

10. The pixel cell circuit according to claim 1 implemented using CMOS compatible components.

11. A neural implant, comprising an array of at least one pixel cell, each of the at least one pixel cell comprising a pixel cell circuit according to claim 1.

* * * * *